Figure 1:
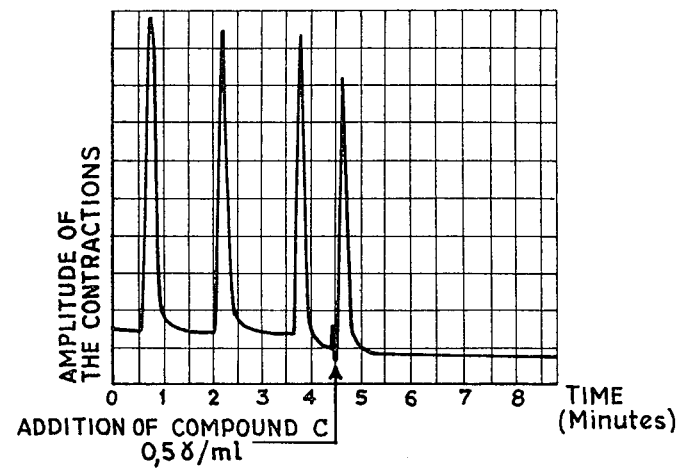

United States Patent [19]

Pinhas

[11] 3,959,359
[45] May 25, 1976

[54] PHENOXYALKYLAMINES, PROCESS FOR THEIR PREPARATION AND THERAPEUTICAL COMPOSITION CONTAINING SAME

[75] Inventor: Henri Pinhas, Paris, France

[73] Assignee: Laboratoires Laroche Navarron, Puteaux, France

[22] Filed: Dec. 11, 1974

[21] Appl. No.: 531,767

Related U.S. Application Data

[63] Continuation-in-part of Ser. No. 211,113, Dec. 22, 1971, abandoned, which is a continuation-in-part of Ser. No. 791,524, Jan. 15, 1969, abandoned.

[30] Foreign Application Priority Data

Jan. 23, 1968   France ................... 68.136966

[52] U.S. Cl. ............... 260/501.18; 260/570.6; 260/570.7; 260/570 R; 260/590 R; 424/316; 424/330
[51] Int. Cl.² ......................... C07C 91/16
[58] Field of Search ......... 260/570.6, 570.7, 501.18; 424/330, 316

[56] References Cited
UNITED STATES PATENTS

| | | | |
|---|---|---|---|
| 3,278,601 | 10/1966 | Moed | 260/570.6 |
| 3,337,628 | 8/1967 | Crowther | 260/570.7 |
| 3,410,901 | 11/1968 | Kunz et al. | 260/570.7 |
| 3,437,731 | 4/1969 | Schmitt | 260/570.6 X |
| 3,501,769 | 3/1970 | Crowther et al. | 260/570.7 |
| 3,513,198 | 5/1970 | O'Brien | 260/570.7 X |
| 3,726,919 | 4/1973 | Wooldridge | 260/501.18 X |
| 3,843,725 | 10/1974 | Pinhas | 260/501.18 X |
| 3,873,620 | 3/1975 | Pinhas | 260/501.18 X |
| 3,892,799 | 7/1975 | Pinhas | 260/501.18 X |

*Primary Examiner*—James O. Thomas, Jr.
*Assistant Examiner*—G. Breitenstein
*Attorney, Agent, or Firm*—Robert E. Burns; Emmanuel J. Lobato; Bruce L. Adams

[57] ABSTRACT

This invention relates to phenoxyalkylamines having the formula:

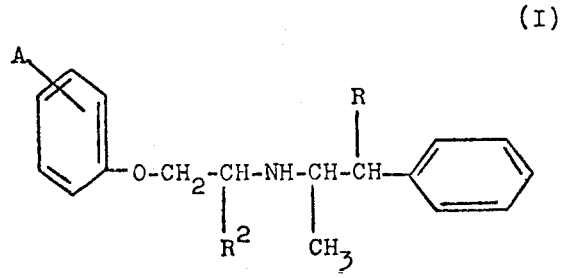

wherein R is a radical selected from the group consisting of hydrogen and hydroxy, $R^2$ is a radical selected from the group consisting of hydrogen and methyl, A is a radical selected from the group consisting of

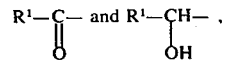

wherein $R^1$ is an alkyl radical having 2–6 carbon atoms.

Said phenoxyalkylamines are coronary vasodilators.

11 Claims, 4 Drawing Figures

PHENOXYALKYLAMINES, PROCESS FOR THEIR PREPARATION AND THERAPEUTICAL COMPOSITION CONTAINING SAME

This application is a continuation-in-part of the application Ser. No. 211,113, Dec. 22, 1971, now abandoned, which is a continuation-in-part of the application Ser. No 791,524, Jan. 15, 1969, now abandoned.

The present invention relates to new phenoxyalkylamines useful, in particular, as coronary vasodilators of formula:

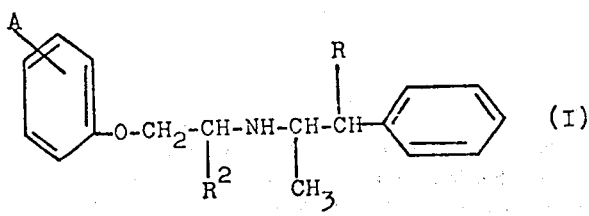   (I)

wherein R is a radical selected from the group consisting of hydrogen and hydroxy, $R^2$ is a radical selected from the group consisting of hydrogen and methyl, A is a radical selected from the group consisting of

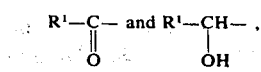

wherein $R^1$ is an alkyl radical having 2–6 carbon atoms.

A preferred class of compounds of formula I are those in which $R^1$ is an alkyl radical having 2–3 carbon atoms.

The compounds may be used either as the free base or as non-toxic acid addition salts such as the hydrochloride, the lactate, the fumarate, the maleate, and the like.

The formula of compounds I always includes at least one asymmetrical carbon. It is understood that the invention includes within its scope the optically active and racemic forms of compounds I.

To prepare compounds (I), an amine of the formula:

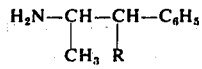   (II)

is condensed with a compound of the formula:

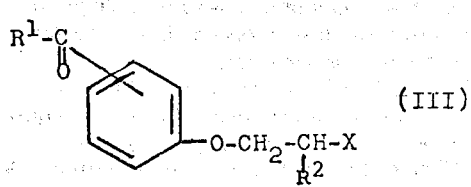   (III)

in which X is a halogen and R, $R^1$ and $R^2$ have the above-defined meanings, and the resulting compound is optionally reduced.

The condensation is advantageously carried out under refluxing conditions, in an alcohol solvent such as ethanol.

Preferably, the reduction step is carried out by using a metal borohydride, such as sodium borohydride or potassium borohydride, in the presence of an alcohol solvent such as methanol.

Starting compound (III) are obtained by reacting a ketophenolic compound of formula:

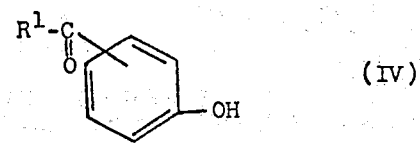   (IV)

with a halogenated compound

   (V)

wherein Y represents a halogen and $R^1$, $R^2$ and X have the above defined meanings.

This reaction is preferably carried out under refluxing conditions in water or in a basic alcohol solution, for example in an ethanol solution containing 5% sodium hydroxide, in a stoichiometric amount with respect to compound IV.

Some of the resulting starting compounds of formula (III) are new compounds.

According to another embodiment, compounds (I) in which $R^2$ is methyl are obtained from compounds of formula:

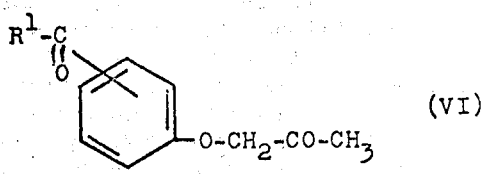   (VI)

which are reacted with an amine (II) to give a reaction product which is reduced into a compound (I) or its hydrogenation product.

It is preferable to react amine (II) with diketone (VI) in a solvent, for example in benzene solution, removing the water formed during the reaction.

When the reaction is carried out in a mild manner, for example by the catalytic route in the presence of palladium-over-charcoal, ketonic compounds (I) are obtained which may then be reduced to their secondary alcohol homologs with a borohydride, such as potassium borohydride or sodium borohydride.

However, it is also possible to obtain the secondary alcohol without an intermediate step, by reducing directly the reaction product of compound (VI) with amine (II) with a reducing agent such as a borohydride.

Starting diketone (VI) is obtained by reacting a compound of formula (IV) with an halogen derivative of formula:

$$X-CH_2-CO-CH_3$$

X being halogen.

This reaction is preferably carried out under refluxing conditions in a basic alcohol solution, for example in an ethanol solution containing the stoichiometric amount of 5% sodium hydroxide with respect to compound (IV).

Examples of the preparation of compounds (I) and of the starting materials from which they may be obtained are given below.

EXAMPLE 1

4-[2-(1-methyl-phenethylamino)-ethoxy]-propiophenone $A = COC_2H_5$ $R = R^2 = H$ a. 4-(2-bromo-ethoxy)-propiophenone is first prepared: to a 60% ethanol solution (200cc) containing para-hydroxy-propiophenone (0.1 mole) and ethylene bromide (0.13 mole) is added, under refluxing conditions, 5% sodium hydroxide (0.1 mole). After 6 hours, the solution is evaporated in vacuo and is then extracted with diethyl ether. It is then washed with dilute sodium hydroxide and with water.

The ether phase is dried, concentrated, and the residue is then distilled: b.p./18 mm of mercury = 202°–207°C, m.p. = 88°C. Yield: 46%.

The following compounds are also prepared as described above:

3-(2-bromo-ethoxy)-propiophenone, b.p./19mm of mercury = 200°–204°C, Yield: 40%,
  and 2-(2-bromo-ethoxy)-propiophenone, b.p./18 mm of mercury = 186°–190°C, Yield: 35%.

b. α-Methyl-phenethylamine (0.02 mole) and 4-(2-bromo-ethoxy)-propiophenone (0.01 mole) dissolved in ethanol (15 cc) are heated under refluxing conditions during 15 hours. The solvent is removed in vacuo. Ether is then added. α-Methyl phenethylamine hydrobromide precipitates out. After suction filtering, the ether phase is abundantly washed with water, and is then dried and concentrated. The oily residue is converted into the hydrochloride using hydrochloric acid in ether. The 4-[2-1-methyl-phenethylamino)-ethoxy]-propiophenone hydrochloride is recrystallized from ethanol (Yield: 70%), m.p. = 191°–192°C.

The above described procedure is used with the ortho and meta derivatives, to give:
  3-[2-(1-methyl-phenethylamino)-ethoxy]-propiophenone,
  Yield: 60%, m.p. = 180°–183°
  2-[2-(1-methyl-phenethylamino)-ethoxy]-propiophenone Yield: 58%, m.p. = 177°C.

EXAMPLE 2

4-[2-(1-methyl-2-hydroxy-phenethylamino)-ethoxy]-propiophenone and its hydrochloride $A = -COC_2H_5$ $R^2 = H$ $R = OH$ 4-[2-(1-methyl-2-hydroxy-phenethylamino)-ethoxy]-propiophenone and its hydrochloride are prepared according to the procedure described in Example 1, substituting, however, α-methyl phenethyl amine with β-hydroxy-α-methylphenethylamine Yield is 75% and the hydrochloride melts at 180°–83°C.

EXAMPLE 3

4-[2-(1-methyl-phenethylamino)-propoxy]-propiophenone and its maleate $A = COC_2H_5$ $R^2 = CH_3$ $R = H$ Para-hydroxy-propiophenone (0.1 mole) and sodium hydroxide (0.1 mole) are dissolved in 80% alcohol (100 cc).

To the refluxing solution are added dropwise 0.12 mole of chloracetone. The reaction mixture is concentrated in vacuo after five hours. The concentrate is extracted with ether and washed with water. The residue is then distilled:
b.p. = 196°–200°C
m.p. = 75°C
Yield: 70%

4(2-oxo-propoxy)-propiophenone (0.02 mole) and α-methylphenethylamine (0.02 mole) in benzene solution are then heated under refluxing conditions. The water formed is removed by means of a Dean-Stark apparatus. The solvent is removed in vacuo and the residue is hydrogenated in the presence of an alcohol solution (40 cc) of 5% Pd/C, during 3 hours. The alcohol is removed. The residue is taken up into ether and is abundantly washed with water. The ether phase is dried and then concentrated. This leaves an oil from which the maleate is obtained in the usual manner; it recrystallizes from acetone-ether, m.p. = 118°–122°C.

EXAMPLE 4

1-(1-hydroxy-propyl)-4[2-(1-methyl-phenethylamino)-ethoxy]-benzene and its hydrochloride.

$A = -CH-C_2H_5$
       $|$
       $OH$ $R = R^2 = H$

Sodium borohydride (0.01 mole) is added to 4-[2-(1-methyl-phenethylamino)-ethoxy]-propiophenone (0.01 mole) dissolved in 90% methanol (15 cc), at a temperature below 10°C. After 4 hours, water is added (100 cc), the reaction mixture is extracted with ether and is then washed with water. The dried ether phase is evaporated. The residue is converted into the hydrochloride in the usual manner. The white crystals recrystallize from alcohol-ether mixture, m.p. = 138°–142°C, Yield: 90%.

EXAMPLE 5

4-[2-(1-methyl-phenethylamino)-ethoxy]-butyrophenone

A = —COC$_3$H$_7$

R$^2$ = H

α-Methyl-phenethylamine (0.02 mole) and 4-(2-bromo-ethoxy)-butyrophenone (0.01 mole) dissolved in ethanol (20 cc) are refluxed during 15 hours. The procedure described in Example 1 is then used. 4-[2-(1-methyl-phenethylamino)-ethoxy]-butyrophenone hydrochloride melts at 195°–197°C.

EXAMPLES 6 and 7

The compounds of formula:

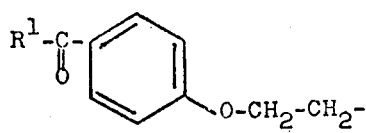

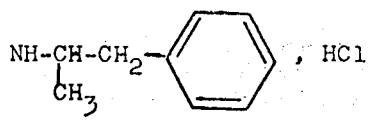

R$^1$ = —(CH$_2$)$_2$—CH$_3$ and
R$^1$ = —(CH$_2$)$_5$—CH$_3$
are prepared as described in EXAMPLE 1, from compounds of formula:

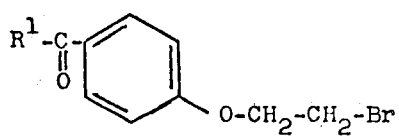

prepared as described in EXAMPLE 1a.

The following table gives the characteristics of the intermediate and final compounds as well as yields.

| Ex. | R$^1$ | Intermediate compound m.p. or b.p | yield | Final compound m.p. | yield |
|---|---|---|---|---|---|
| 6 | —(CH$_2$)$_2$—CH$_3$ | m.p.=92°C | 61 % | 195–197°C | 53 % |
| 7 | —(CH$_2$)$_5$—CH$_3$ | b.p./2mm= 205–210°C | 43 % | 186–189°C | 58 % |

EXAMPLES 8 and 9

The compounds of formula:

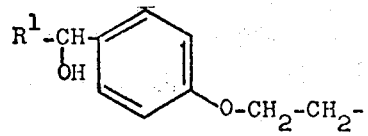

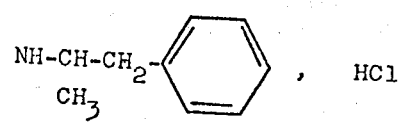

R$^1$ = —(CH$_2$)$_2$ CH$_3$ and
R$^1$ = —(CH$_2$)$_5$—CH$_3$
are prepared as described in EXAMPLE 4 from the compounds obtained in EXAMPLES 6 and 7.

The following table gives the melting points and yields of said compounds.

| Ex. | R$^1$ | m. p. | yield |
|---|---|---|---|
| 8 | —(CH$_2$)$_2$—CH$_3$ | 131–133°C | 92 % |
| 9 | —(CH$_2$)$_5$—CH$_3$ | 128–130°C | 89 % |

The results of toxicological and pharmacological tests carried out with compounds (I) will be given below.

1. Acute toxicity

The oral LD$_{50}$ in mice of said materials is of the order of 200 mg/kg to 500 mg/kg and is of the same order of magnitude in rats.

2. Coronary dilator activity

The coronary dilator activity was studied according to Langendorff's method on the isolated heart.

The tests were carried out on the hearts of young Fauve de Bourgogne (about 1.5 kg) rabbits. The hearts were rapidly taken out and maintained in surviving condition by perfusion of a physiological (Tyrode type) liquid heated at 37°C and oxygenated under a constant pressure of 50–60 cm of water. The heart was perfused countercurrently.

Volumetric determinations of the coronary rate of flow were then recorded at thirty second intervals.

After stabilization of the basic rate of flow, the test compound, dissolved in physiological saline solution, was injected in the perfusion liquid, in a volume of from 0.05 to 0.2 ml.

The following compounds were studied:

4[2-(1-methyl-phenethylamino) ethoxy]-propiophenone (example 1).

1-[1-hydroxy-propyl]-4-[2(1-methyl-phenethylamino) ethoxy]benzene (example 4).

4[2(1-methyl phenethylamino)-ethoxy]-butyrophenone (example 5).

In the same heart, increasing dosages of all three compounds were tested by injecting alternatively a predetermined dose for each one of the three compounds.

Each injection was made 4–5 minutes after a stable rate of flow was attained.

The results of the tests carried out with two rabbits A and B are reported in the table I.

The above results demonstrate the superiority of the compound according to the invention. This compound is 2.5 to 4.5 times more efficient than Isoxsuprine.

b. UTERINE RELAXANT ACTIVITY

The uterine relaxant activity has been extensively investigated in the case of Isoxsuprine. It was demonstrated that this activity is essentially due to beta receptor activation (International Conference on Duvadilan, May 1962, Duphar).

The study was conducted on rat uterus, using the following compounds:

Compound of Example 1 : 4-[2-(1-methyl phenethylamino)-ethoxy]-propiophenone (hydrochloride).

TABLE I

| amount of compound injected (γ) | 2 | 5 | 10 | 20 | 25 | 40 | 50 | 80 | ED 50 |
|---|---|---|---|---|---|---|---|---|---|
| Ex.1 A | | 12% | 34% | 47% | | 50% | | 80.5% | 27 γ |
| B | | | 8% | 37% | | 50% | | 62% | 44 γ |
| Ex.4 A | 10 | 30% | 33% | 67% | | 93% | | | 11 γ |
| B | | | 11% | 30% | | 55% | | 78% | 35 γ |
| Ex.5 A | | | | 21% | 57% | | 64% | | 24 γ |
| B | | | | 16% | 39% | | 50% | | 45 γ |

A : First heart
B : Second heart

The tests compounds of the invention produce an increase of 50% of the original coronary rate of flow at a dosage comprised within the range of 11 to 45 γ.

The pharmacological activity of the present compounds has been compared with the activity of known N-phenoxyalkyl N-phenylalkylamines which are not substituted on the phenoxy moiety with a radical

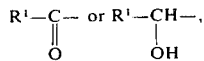

$R^1$ being an alkyl having 2–6 carbon atoms.

a. CORONARY DILATOR ACTIVITY

The activity of 1-[1-hydroxy-propyl] 4-[2(1-methyl-phenethylamino) ethoxy]benzene (example 4) was compared with the activity of Isoxsuprine [1-(p-hydroxyphenyl)-2-(1-methyl-2 phenoxyethylamino) propanol-1], disclosed in U.S. Pat. No. 3,278,601.

The tests were carried out as above with three rabbits.

The results of the tests are reported in the Table II.

(Compound A)

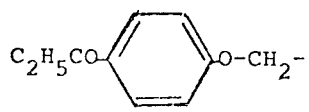

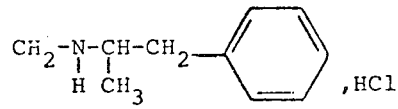

Compound of Example 4 : 1-(1-hydroxypropyl)-4-[2-(1-methyl-phenethylamino)-ethoxy]-benzene, (hydrochloride) (Compound B)

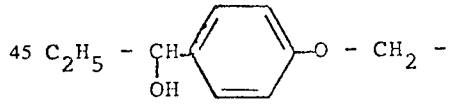

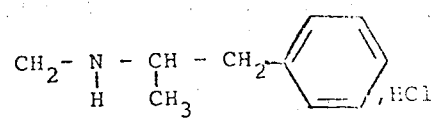

TABLE II

| Amount of compound injected | HEART No. 1 Compound of the invention | HEART No. 1 Isoxsuprine | HEART No. 2 Compound of the invention | HEART No. 2 Isoxsuprine | HEART No. 3 Compound of the invention | HEART No. 3 Isoxsuprine |
|---|---|---|---|---|---|---|
| 10 γ | | | + 33 % | | | |
| 20 γ | | | + 50 % | + 17 % | + 17 % | |
| 40 γ | + 33 % | + 8 % | + 80 % | + 43 % | + 46 % | 0 % |
| 80 γ | + 54 % | + 20 % | | + 60 % | + 50 % | + 17 % |
| 160 γ | + 78 % | + 50 % | | | + 75 % | + 33 % |
| 320 γ | | | | | | + 50 % |
| 640 γ | | | | | | + 75 % |
| ED$_{50}$ | 68 | 180 | 18 | 54 | 64 | 290 |
| ED$_{50}$ compound of the invention / ED$_{50}$ Isoxsuprine | 1/2.5 | | 1/3 | | 1/4.5 | |

Isoxsuprine (Compound I of U.S. Pat. No. 3,278,601) (Compound C)

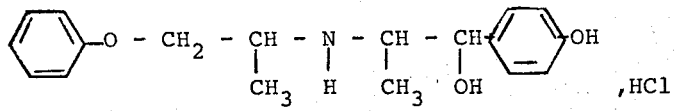

Compound IV of U.S. Pat. No. 3,278,601 (Compound D)

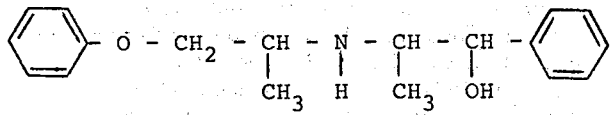

1. Material and method

The conventional method of De Jalon, Bayo and De Jalon (1945). Farmacoter. act. 3, 313 — also reported in the book : "Pharmacological Experiments on Isolated Preparations" by the staff of the Department of Pharmacology, University of Edinburgh, published by E. & S. Livingstone Ltd, London — was used, the pharmacological investigation being conducted on the uterine cornuae of female rats (Sprague Dawley strain) kept alive in a survival liquid.

A tank containing Tyrode's solution is maintained at a constant temperature of 32°C. The test organ is suspended to a strain gauge for the purpose of recording the contractions on a potentiometric recorder. The uterine cornuae are taken from non-gravid puberal female rats having an average weight of 160 g.

The day prior to the test, the animals are administered a di-ethyl-stilboestrol injection. Postmortem, the cornuae are isolated as rapidly as possible and a 15 mm fragment from which the connective tissue has been removed is placed in the experimental cell.

2. Results

During oestrum, regular spontaneous contractions (FIG. 1) are noted; such oscillations are stable within 30–60 minutes, after washing several times with suitably oxygenated Tyrode's solution.

Addition to the bath of uterine relaxant material produces, at a low dosage, a total inhibition of such spontaneous contractions.

Figure 2:
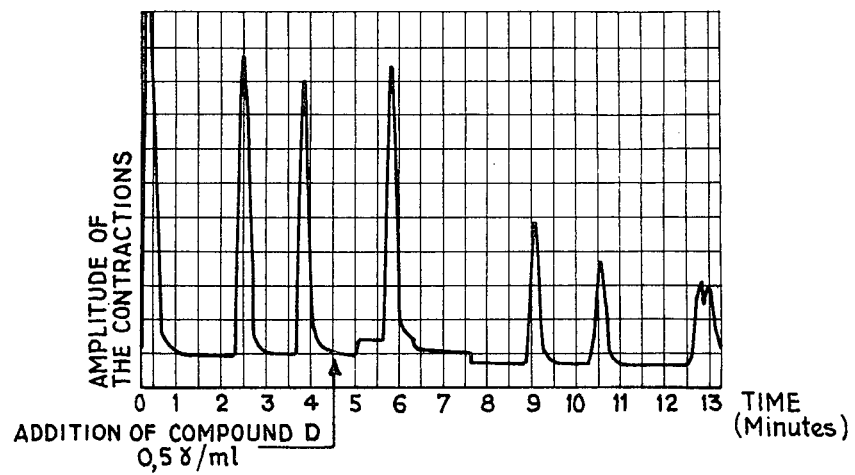

In all such tests, Isoxsuprine (Compound C) was found to have a total uterine relaxant action at a dosage of 0.5 γ/ml of bath (FIG. 1); compound D was found to have a reduced uterine relaxant effect at the same dosage level (70% inhibition, FIG. 2).

Figure 3:
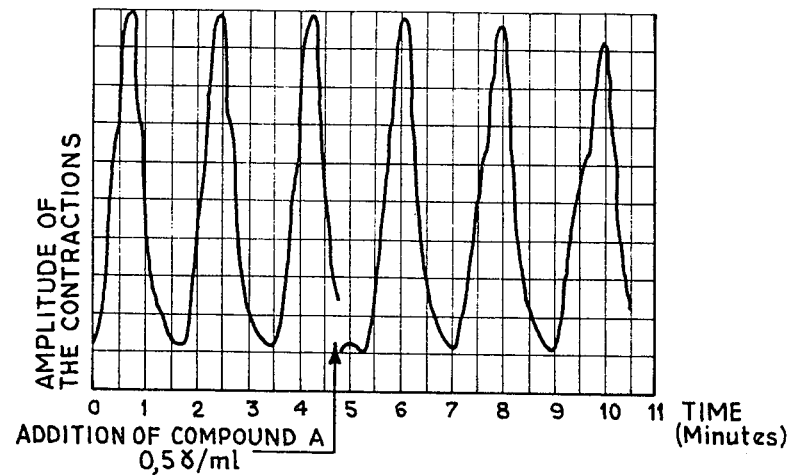
Figure 4:
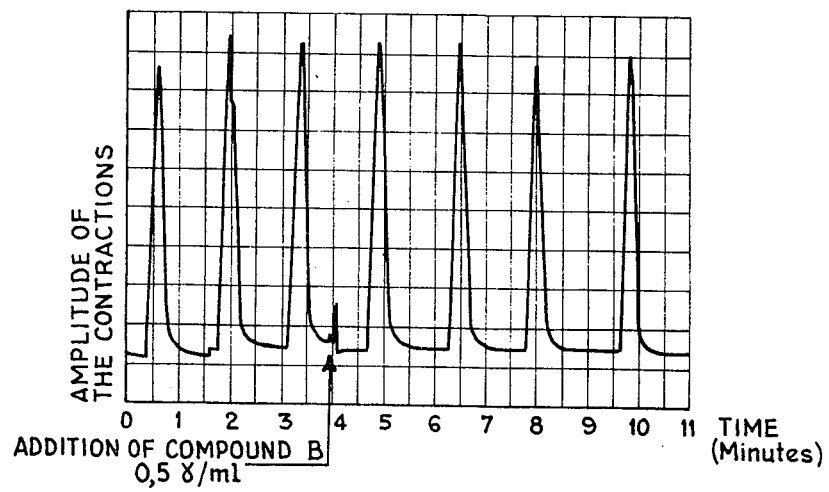

The compounds of this invention (Compounds A and B) have absolutely no uterine relaxant effect at this dosage level of 0.5 γ/ml (FIGS. 3 and 4).

| Compounds | % Inhibition |
|---|---|
| Compound A | 0 |
| Compound B | 0 |
| Compound D | 70 |
| Isoxsuprine | 100 |

3. Conclusion

The compounds of this invention are ineffective on the spontaneous contraction of the uterus of female rats at a dosage of 0.5 γ/ml of bath.

The compounds of U.S. Pat. No. 3,278,601 are found to have a high uterine relaxant effect at the same dosage level.

c. STUDY OF THE BETA-STIMULANT ACTION

A comparison was made of the beta-stimulant action of the same compounds as used in the above experiment.

1. Material and method

The duodenum of rats (Sprague Dawley strain) weighing about 150 g is taken immediately post-mortem. The test organ is immediately placed in a suitable cell for the isolated organ (oxygenated Tyrode's solution maintained at a temperature of 37°C).

Addition of acetylcholine (0.1 γ/ml) to the bath induces a contraction of the organ which is immediately transmitted via a strain gauge to a potentiometric recording device.

Addition of a beta-stimulant material causes inhibition of this concentration.

2. Results and conclusion

A comparison was made between the actions of various materials on cholinergic contractions.

At the dosage of 0.1 γ/ml of bath, Isoxsuprine (Compound C) and Compound D are found to possess a highly beta-stimulant action.

At the same dosage level, the compounds of this invention (Compounds A and B) are found to possess only a slight beta-stimulant effect.

Said results are set forth in the following Table:

| Compounds | % Inhibition |
|---|---|
| D | 100 |
| C (Isoxsuprine) | 100 |
| A | 15 |
| B | 15 |

The pharmacological data obtained with Isoxsuprine confirm also the known properties of Isoxsuprine (or Duvadilan).

A difference of activity is readily apparent between the compounds of the present invention and those disclosed in U.S. Pat. No. 3,278,601, which difference is also reflected in a different therapeutic applicability, the compounds of U.S. Pat. No. 3,278,601 being essentially uterine relaxants and peripheral irrigators, whereas the compounds of this invention are coronary vasodilators.

In addition, in view of its beta-stimulant properties, Isoxsuprine increases ventricular stimulability and increases also the possible occurrence of extrasystoles, particularly ventricular extrasystoles, the frequency and severity of which in the course of coronary insufficiency conditions are well known.

The compounds of this invention do not exhibit this drawback. They do not increase the work of the heart. They have a very slight peripheral alpha-blocking effect and, thus, decrease the potential occurrence of orthostatic hypotension.

The difference of activity is still more readily apparent between the compounds of the invention and the compounds disclosed in U.S. Pat. No. 3,437,731 (N-(2-phenyl-1-methyl-ethyl)-2-phenoxy-1-methyl-ethylamine), i.e. phenoxyalkylamines which are unsubstituted on the phenoxy moiety. These compounds are uterus relaxants and exhibit a reduced vasodilator activity compared to Isoxsuprine.

Thus it is clear that the presence of the radical A on the phenoxy moiety in the compounds of the invention confers to these compounds unexpected and advantageous properties.

The results of clinical experiments are given below.

The compound prepared in example 4 (1-(1-hydroxypropyl)-4-[2-(1-methyl-phenethylamino)-ethoxy]-benzene hydrochloride) was experimented in four different Cardiology Services. 211 patients were treated with this compound. These patients suffered from different anginose states or from ichemic diseases of the heart (coronary failures or after-effects of infarct). In these experiments, it has been found no contra-indication and no modification of the cardiac frequency and of the arterial pressure. Therefore the tolerance is excellent.

Favourable results were obtained with 172 patients (81.5%).

It follows from these tests that compounds (I) are useful in human therapeutics as coronary vasodilators.

Therefore, the present invention provides also a method for the treatment of coronary insufficiency which comprises administering to a patient a therapeutically effective quantity of a compound of the invention.

In such applications, compounds (I) are advantageously administered orally at a dosage of 100 to 600 mg of active principle per 24 hours.

All the formulations suitable for this route of administration may be used, the active principle being admixed with a pharmaceutically acceptable vehicle or excipient. An example of such a formulation is quoted:

|  | Average dose | Strong dose |
|---|---|---|
| Tablets containing each | 50 mg | 100 mg |
| Excipients: Talc<br>Lactose<br>Mg stearate, q.s. to make 1 tablet. | | |

Having now described my invention what I claim as new and desire to secure by Letters Patent is:

1. A compound selected from the group consisting of phenoxyalkylamines of the formula:

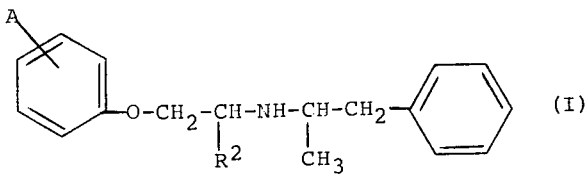

wherein $R^2$ is a radical selected from the group consisting of hydrogen and methyl and A is a radical selected from the group consisting of

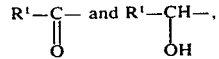

wherein $R^1$ is an alkyl radical having 2–6 carbon atoms and the non-toxic acid addition salts thereof.

2. A compound as claimed in claim 1, wherein $R^1$ is an alkyl radical having 2-3 carbon atoms.

3. 4-[2-(1-methyl-phenethylamino-ethoxy]-propiophenone and its non-toxic acid addition salts.

4. 4-[2-(1-methyl-phenethylamino)-propoxy]-propiophenone and its non-toxic acid addition salts.

5. 1(1-hydroxy propyl)-4-[2-(1-methyl phenethylamino)-ethoxy]-benzene and its non-toxic acid addition salts.

6. 4-[2-(1-methyl-phenethylamino)-ethoxy]-butyrophenone and its non-toxic acid addition salts.

7. A method for the treatment of coronary insufficiency which comprises administering to a patient a therapeutically effective quantity of a compound selected from the group consisting of phenoxyalkylamines of the formula:

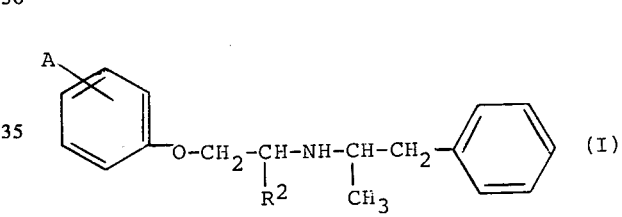

wherein $R^2$ is a radical selected from the group consisting of hydrogen and methyl and A is a radical selected from the group consisting of

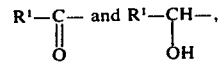

wherein $R^1$ is an alkyl radical having 2–6 carbon atoms and the non-toxic acid addition salts thereof.

8. A method as claimed in claim 7, which comprises administering orally from 100 to 600 mg of compound per 24 hours.

9. A composition for the treatment of coronary insufficiency which comprises a therapeutically effective quantity of a compound as claimed in claim 1, and a pharmaceutically acceptable vehicle.

10. A composition for the treatment of coronary insufficiency which comprises a therapeutically effective quantity of a compound as claimed in claim 2, and a pharmaceutically acceptable vehicle.

11. A composition for the treatment of coronary insufficiency which comprises a therapeutically effective quantity of a compound as claimed in claim 5, and a pharmaceutically acceptable vehicle.

* * * * *